Figure 3:
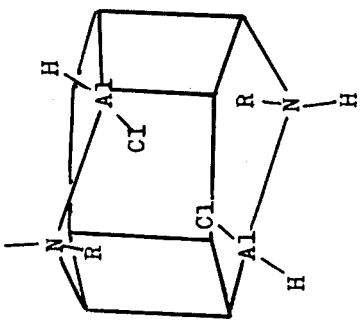

United States Patent [19]

Dozzi et al.

[11] 4,032,553

[45] June 28, 1977

[54] ALUMINIUM HYDRIDE OLIGOMER DERIVATIVES AND PROCESS FOR THE PREPARATION THEREOF

[75] Inventors: Giovanni Dozzi; Giovanni Perego, both of Milan; Carlo Busetto, Padova, all of Italy

[73] Assignee: Snam Progetti S.p.A., Milanese, Italy

[22] Filed: July 1, 1975

[21] Appl. No.: 592,247

[30] Foreign Application Priority Data

July 1, 1974 Italy .................................. 24662/74

[52] U.S. Cl. .......................... 260/448 R; 260/2 M
[51] Int. Cl.² ......................................... C07F 5/06
[58] Field of Search ...................... 260/448 R, 2 M

[56] References Cited

UNITED STATES PATENTS

| | | | |
|---|---|---|---|
| 3,245,976 | 4/1966 | Marconi et al. | 260/94.3 |
| 3,311,604 | 3/1967 | Marconi et al. | 260/94.3 |
| 3,505,246 | 4/1970 | Ehrlich et al. | 260/2 M |
| 3,781,318 | 12/1973 | Corbellini et al. | 260/448 R |

OTHER PUBLICATIONS

Ehrlich et al. (II) Inorg. Chem. 3 (1964) p. 628–630.

*Primary Examiner*—Arthur P. Demers
*Attorney, Agent, or Firm*—Ralph M. Watson

[57] ABSTRACT

The present invention provides novel oligomer derivatives of aluminum hydride having the general formula:

$$(XAlNR)_x (XYAl)_y (NHR)_y.$$

3 Claims, 3 Drawing Figures

ALUMINIUM HYDRIDE OLIGOMER DERIVATIVES AND PROCESS FOR THE PREPARATION THEREOF

The present invention relates to novel oligomer derivatives of aluminium hydride as well as the process for the preparation thereof. More particularly the inventive object is constituted by a novel class of oligomer derivatives having the following general formula

in which R is an aliphatic, aromatic or cycloaliphatic hydrocarbon radical, X and Y, the same or different, mean hydride hydrogen and/or halogen atoms bound directly to aluminium, the number of halogen atoms being lower than or equal to $x + 2y$ and the difference to $x + 2y$ being constituted by hydride hydrogen atoms; the sum $(x + y)$ is a whole number lower than or equal to 10, $y$ being a whole number other than zero: the hydride hydrogen atoms mean hydrogens bound directly to aluminium, and can be determined according to known analytical methods.

In the above said formula $x$ and $y$ do not necessarily refer to repeated imine or amine units having the same composition.

A characteristic of the inventive compounds, as it is possible to draw from the general formula, is given by the atomic ratios $N/Al = 1$, and $(X + Y)/Al > 1$.

According to a more specific formulation, the inventive compounds are mono- or polycyclic oligomer derivatives characterized by condensed rings containing aluminium and nitrogen atoms. For instance they derive from 4 and/or 6 term rings, exemplified by the FIGS. I, II and III

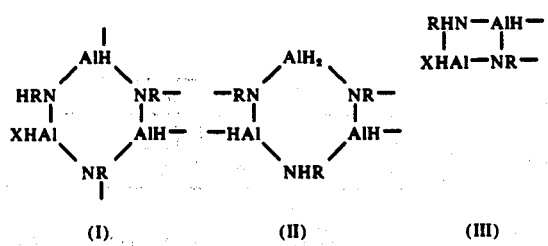

in which the dangling valences may be partially or totally saturated by hydrogen or halogen and/or may give rise, through a condensation with other rings of the same type or of the type IV and V

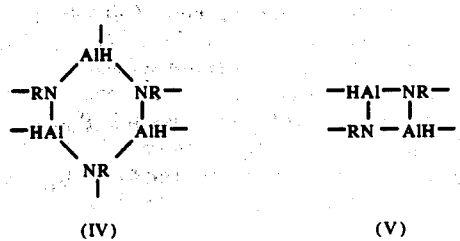

to "cage" tridimensional structures.

The above general formula comprises also compounds having an open cage tridimensional structure resulting from the condensation of the aforementioned cycles with imine units and/or 4 and/or 6 term open cycles of the type, for istance,

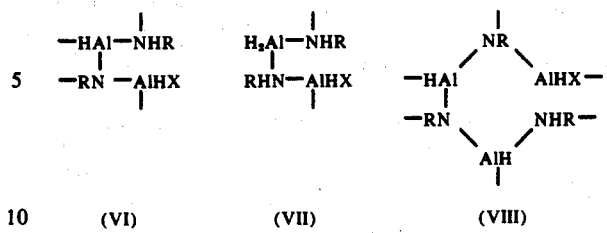

The above general formula moreover comprises compositions in which the groups AlXY and NHR may be near or far in the molecule so that no intereaction is possible without any substantial structural rearrangement.

Aluminium polyimine derivatives and also methods for the preparation thereof are known.

In fact the reaction between ether-dioxane solutions of AlH₃ and methyl amine has been reported by Wiberg and May in "Z. Naturforsch 10b, 232 (1955)": according to these authors it is possible to obtain a substance insoluble in the organic solvents, which was given a polymer structure corresponding to a poly (N-methyl-iminoalane) containing repeated unities of the type

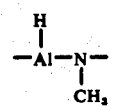

More recently Ehrlich and May, in U.S. Pat. No. 3,505,246, reported the preparation of similar compounds, they named poly (N-ethylalazenes) and poly (N-methylalazenes) and define as long chain linear polymer compounds, in which the polymerization degree of the unity HAl — NR is at least 10.

We have now found it is possible to synthetize oligomer products as abovesaid, which constitute a first object of the present invention, through a process, which is a further object of the invention, consisting in reacting aluminium hydrides, complexed with Lewis bases, with primary amines, eventually in the presence of an aluminium halide (in the case of the preparation of derivatives containing halogen atoms) the reaction being carried out under the conditions defined hereinafter.

Examples of amines to be used in the preparation of the inventive products are iso-propyl-amine sec-butyl-amine, isobutyl-amine, tert-butyl-amine, cyclo-hexyl-amine.

Interesting applications are also to be awarded to products derived from the substitution, either partial or total, of hydride hydrogen with atoms or different groups such as amine, hydroxil, alkoxy, mercaptan groups obtained, for instance, by reacting the products referred to with controlled amounts of primary amines, also different from the ones constituting N-alkylimino alanes, secondary amines, nitriles, water, alcohols, hydrogen sulphide, mercaptans, etc.

The reaction is carried out in a hydrocarbon or in an ether solvent, or anyhow in the presence of solvents which do not contain functional groups able to react with the hydride hydrogens, at temperatures ranging from $-20°$ C to the solvent boiling temperature: where this temperature is necessary, the mixture ebullition must be not prolonged.

Obtaining the inventive products is particularly favoured by the following factors:

a. low temperatures which avoid intramolecular rearrangements and/or intramolecular reactions that might give rise to cyclization;

b. replacement of some hydride hydrogens with halogens that stabilize the open structures;

c. use of amines containing alkyl radicals having branchings, in alpha or beta position with respect to nitrogen, characterized by a high steric hindrance, such as, for istance, ter-butyl-amine.

The oligomer derivatives, according to the present invention, can be used as components of catalyst systems for polymerisations or reductions of several organic substrates as shown in copending application Ser. No. 592,249.

EXAMPLE 1

Under a nitrogen atmosphere, a solution of t-butyl-amine (180 mmoles) in diethyl ether (50 ml) was slowly added to a stirred solution of $AlH_3 \cdot N(CH_3)_3$ (180 mmoles) in diethyl ether (200 ml). The reaction occurred through a hydrogen development. The reaction mixture was kept stirring for 4 hours and resting over 50 hours.

Then, after having filtered insoluble material traces, the clear solution was cooled at $-78°$ C, crystals formed, that were separated by a cold filtration.

They were constituted by tetra (N-tert-butyliminoalane).

Solvent and trimethylamine were separated from the remaining solution through an evaporation under vacuum, and the white solid residual was dried (10 h, room temperature, $10^{-3}$ mmHg) to give 6.5 g of crystaline product.

| Analysis: | Al | N | H active |
|---|---|---|---|
| Found | 26.39 % | 13.39 % | 12.44 meq/g |
| Calculated $(HAlNC_4H_9)_3$ | | | |
| $(H_2AlNHC_4H_9)$ | 27.08 % | 14.06 % | 12.55 meq/g |

Figure 1:
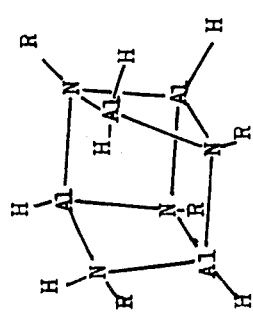

The physical-chemical determinations showed, as to this product, the molecular structure reported in FIG. 1.

The molecular weight, determined in ethyl ether at boiling, was 440 close to the calculated value that is 398.5. The $^1H$ NMR spectrum in benzene showed three signals due to the protons of methyl groups belonging to amine radicals at $\tau$ 8.63, $\tau$ 8.57 and $\tau$ 8.63 whose reciprocal intensity was 1 : 1 : 2, according with different steric situations of nitrogen atoms.

The resonance at $\tau$ 8.57 was assigned to the protons of t-butyl radical or nitrogen atoms bound to three groups AlH. The resonance at $\tau$ 8.39 was assigned to the radicals on two nitrogen atoms bound to two groups AlH and to one group $AlH_2$. At last the signals at $\tau$ 8.63 was assigned to the groups $NH$-tert-$C_4H_9$.

The mass spectrometry showed ions $(M - CH_3)^+$ at m/e 391 deriving from tetra (N-tert-butyliminoalane) in which tert-$C_4H_9HN - (HAIN \text{ tert} . C_4H_9)_3 - AlH_2$ changed by a high temperature heating, at different rates according to the value thereof. At last the I.R. spectrum showed a band $\nu$ Al-H at a maximum at 1850–1860 cm$^{-1}$ agreeing with the presence of tetracoordinated aluminium atoms.

EXAMPLE 2

Under a nitrogen atmosphere a solution of $AlCl_3$ (348 mmoles) in diethyl ether (150 ml) was added, drop by drop, to a stirred suspension of NaH (1045 mmoles) in ethyl ether-hexane (30 ml in a 60 : 40 ratio) added with little amount of $AlEt_3$ (10 mmoles), at the solvent boiling temperature. At beginning the reaction mixture was heated externally, then the reflux temperature was maintained by regulating the addition rate of the $AlCl_3$ solution.

The $AlCl_3$ addition was carried out in two stages. After the addition of the amount corresponding to the synthesis "in situ" of $NaAlH_4$ according to the reaction

$$4NaH + AlCl_3 \rightarrow NaAlH_4$$

the reaction mixture was stirred for 1 hour at boiling temperature. There the remaining amount of $AlCl_3$ was added and, at end, the whole was still kept refluxing for two hours. The complete reaction between $AlCl_3$ and $NaAlH_4$ to give $AlH_3$ according to the reaction

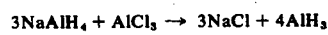

$$3NaAlH_4 + AlCl_3 \rightarrow 3NaCl + 4AlH_3$$

was ascertained by the chlorine determination in the solution: chlorine was absent. Then a solution of iso-propylamine (325 mmoles) in diethyl ether (50 ml) was added, drop by drop, to the reaction mixture. Hydrogen developed. After having been stirred at reflux temperature, the reaction mixture was filtered, from the solution the solvent was evaporated under vacuum and substituted by diethyl ether. The ether solution was cooled at 5° C. After 50 hours, the formed crystals were separated through a decantation from the mother liquid and dried under vacuum (10 hours, room temperature, $10^{-3}$ mmHg) to give 4.5 go of white crystalline product.

| Analysis: | Al | N | H active |
|---|---|---|---|
| Found | 29.80 % | 15.81 % | 18.40 meq/g |
| Calculated $(HAlNC_3H_7)_3$ | | | |
| $(H_2AlNHC_3H_7)_3$ | 31.25 % | 16.22 % | 18.55 meq/g |

Figure 2:
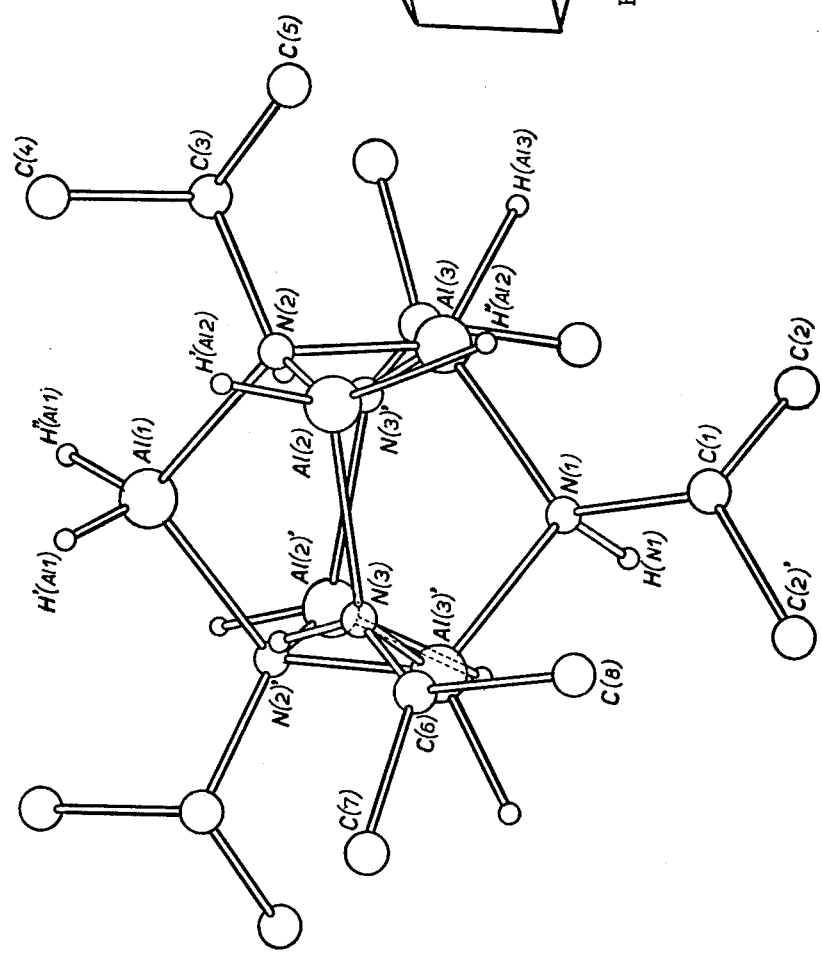

The product obtained thereby was analyzed, as to the molecular structure, at X-ray diffraction: the spectrum is reported in FIG. 2.

EXAMPLE 3

A solution of $LiAlH_4$ (109 mmoles) in diethyl ether (100 ml) was added to a suspension of iso-$C_3H_7NH_2 \cdot HCl$ (104 mmoles) in diethyl ether (40 ml) stirred at room temperature. At end, the whole was heated at the boiling temperature over 2.5 hours. LiCl was filtered and the solution was concentrated by evaporating the solvent under a reduced pressure and added with hexane (90 ml). There was again a precipitation of little insoluble material, which was removed by filtration.

On the solution were calculated the following atomic ratios

| N/Al = 0.967 | H active/Al = 1.30 |
|---|---|

The solution of the compound thus obtained was then added with an ether solution of HCl in such an amount corresponding to an atomic ratio Cl/Al = 0.3.

The solvent was completely removed by evaporating under reduced pressure and replaced by n-hexane to give a clear solution, for which

| N/Al = 0.975 | H active/Al = 0.969 | Cl/Al = 0.30 |
|---|---|---| in agreement with the substitution of hydride hydrogen atoms with chlorine atoms according to FIG. 3.

What we claim is:
1. A compound of the formula of FIG. 1 wherein R is tert-butyl.
2. A compound of the formula of FIG. 2.
3. A compound of the formula of FIG. 3. wherein R is isopropyl.